United States Patent

Colin

[11] Patent Number: 5,594,183
[45] Date of Patent: Jan. 14, 1997

[54] PROCESS FOR METERING, IN PARTICULAR MICROVOLUMES OF A LIQUID; APPLICATION TO OBTAINING CONTROLLED DILUTIONS, ESPECIALLY NANOMOLAR DILUTIONS

[75] Inventor: Bruno Colin, Tassin La Demi-Lune, France

[73] Assignee: Bio Merieux, L'Etoile, France

[21] Appl. No.: 272,398

[22] Filed: Jul. 26, 1994

[30] Foreign Application Priority Data

Jul. 28, 1993 [FR] France .................... 93 09517

[51] Int. Cl.⁶ .................................... G01N 1/14
[52] U.S. Cl. ............................ 73/864.52; 73/864.34
[58] Field of Search ............. 73/864.01, 864.03, 73/864.11–864.13, 864.15, 864.22, 864.52, 864.34

[56] References Cited

U.S. PATENT DOCUMENTS

| 1,678,540 | 7/1928 | Trenner | 73/864.12 |
| 3,626,762 | 12/1971 | Gilford | 73/864.52 |
| 4,537,747 | 8/1985 | Castaneda | 73/864.52 |
| 5,221,311 | 6/1993 | Rising et al. | 73/864.52 |

FOREIGN PATENT DOCUMENTS

| 0351761 | 1/1990 | European Pat. Off. |
| 0508530 | 10/1992 | European Pat. Off. |
| 1598629 | 12/1970 | Germany |
| 2717963 | 11/1978 | Germany |
| 652144 | 10/1985 | Switzerland |

*Primary Examiner*—Robert Raevis
*Attorney, Agent, or Firm*—Oliff & Berridge

[57] ABSTRACT

A capillary cavity is provided in communication with a liquid bath container. The cavity is metered with a predetermined quantity of a liquid by a process that includes: (a) providing at least one capillary cavity, which outwardly emerges via an introduction orifice and is dimensioned such that the liquid cannot enter or leave the cavity spontaneously; (b) providing a bath of the liquid; (c) evacuating the cavity, initially free of any liquid, in order to bring its internal pressure to a value that is less than a pressure prevailing above the liquid bath; (d) connecting the interior of the capillary cavity, which is at least partially evacuated, to the liquid bath via the introduction orifice, thereby filling the cavity; (e) separating the filled capillary cavity from a remainder of the liquid bath; (f) emptying the capillary cavity which is filled and separated from the liquid bath via the introduction orifice. The method and device have applications including, for example, diluting a precise amount of liquid with a diluent.

21 Claims, 4 Drawing Sheets

PROCESS FOR METERING, IN PARTICULAR MICROVOLUMES OF A LIQUID; APPLICATION TO OBTAINING CONTROLLED DILUTIONS, ESPECIALLY NANOMOLAR DILUTIONS

BACKGROUND OF THE INVENTION

The present invention relates to metering, that is to say, sampling and releasing a predetermined or controlled quantity of a liquid or fluid. More precisely, the invention concerns metering microvolumes of a liquid, that is to say, sampling and releasing of microquantities, for example, volumes of the order of a few microliters or of a few fractions of a microliter of a liquid.

The invention finds application, in particular, for obtaining controlled and infinitesimal dilutions, for example nanomolar dilutions.

There is currently no way of truly metering microquantities of a liquid under suitable conditions of precision, repeatability and reliability. For this purpose, pipettes or micropipettes are generally used, for example pipettes marketed by the company GILSON under the brand name GILSON 90403 P1000, which sample a predetermined volume of liquid by applying a reduced pressure which is calibrated by the course of a plunger, and release the volume sampled by applying an overpressure above the plunger.

Such a micropipette is, for example, described in document DE-A-1,598,629.

The precision of micropipettes is limited by the surface tension of the liquid sampled, the capillary forces exerted inside and outside the wall of the pipette, and attachment or retention of microdroplets on the end of the pipette.

SUMMARY OF THE INVENTION

The object of the present invention is to overcome the current limitations of the various existing devices or systems for metering microquantities, by allowing sampling then release of volumes less than one microliter, under good conditions of precision, reliability and repeatability.

In its most general form, one aspect of the present invention involves a metering process for measuring predetermined amounts of liquid especially for metering microvolumes. The process includes the following steps:

(a) At least one capillary cavity is provided which is capable of containing the liquid to be metered, for example closed or sealed at one end, the outwardly emerging orifice of which is used both for introducing and emptying said liquid, and is dimensioned such that the liquid cannot enter or leave the cavity spontaneously. Advantageously, the cross section of the introduction and/or emptying orifice is chosen to be less than the mean cross section of the capillary cavity. For an internal volume of the capillary cavity which is at least equal to the volume to be metered, the residual internal pressure, controlled at the end of step (c) hereinbelow, controls the obtaining of a predetermined quantity of the liquid, for example of the liquid to be diluted, at the end of step (d) hereinbelow.

(b) A bath of the liquid to be metered, for example of the liquid to be diluted, is also provided.

(c) The capillary cavity, initially free of any liquid, is evacuated at least partially in order to bring its residual internal pressure to a predetermined value which is less than that prevailing above the liquid bath during step (d), especially atmospheric pressure.

(d) The interior of the capillary cavity, which is partially evacuated, is connected via the introduction and emptying orifice to the liquid bath, which is, in particular, under atmospheric pressure, thereby filling the cavity with the liquid, for example the liquid to be diluted.

(e) The capillary cavity filled with liquid, or more precisely its support incorporating it, is separated from the rest of the liquid bath, either by extracting the support from the liquid bath or by emptying or removing the liquid bath from around the support.

(f) The liquid filling the capillary cavity, separated from the liquid bath, is emptied by any suitable device, and preferably by pressure reduction, for example into or within another liquid bath, namely the diluent.

The term "capillary cavity" is taken to mean any empty space within a solid support, comprising one or more capillary channels extending over a certain length, with any suitable shape, regular or irregular, for example straight or spiralled, and whose cross section, which is for example circular, has dimensions (especially a diameter) such that any liquid is introduced therein or removed therefrom while forming a meniscus or liquid/gas interface contained in the channel. This capillary cavity is, by its very nature, closed on one side and open on the other side in a single or multiple orifice, via which, according to the present invention, the liquid to be metered is both introduced and emptied, in particular, a capillary cavity in the sense of the present invention, any conduit which is closed on one side and open on the other, within which a liquid can flow in capillary regime, that is to say in the manner of a "plunger", without making a liquid/gas interface in the length direction of the capillary cavity. Preferably, this cavity has substantially the same transverse section, both in shape and dimensions, from one end of its length to the other.

The effective dimensions of this capillary cavity, that is to say, those necessary to obtain a capillary flow within it, depend on many parameters, such as viscosity of the liquid entering the cavity, temperature and surface tension of said liquid, condition and nature of the internal surface of the cavity, so that it is easy for a person skilled in the art to determine, by routine tests and for controlled operating conditions, the dimensions such as diameter below which a capillary flow regime is set up for a given liquid to be metered. Preferably, these routine tests will be carried out by placing the interior of the cavity in communication via the introduction/emptying orifice with a bath of the liquid to be metered, this being with a substantially isobaric relationship between the gaseous interior of the cavity and the bath of the liquid, and for various transverse dimensions (or diameters) of the cavity.

As regards the solid support, this may be a free support, such as a ball, or a fixed support, for example mounted on the wall of the container for receiving the liquid bath.

By virtue of the present invention, if the volume of the capillary cavity is at least equal to the volume to be metered, the quantity filling said cavity during step (d) is a function of, and can be controlled by, the only residual internal pressure at the end of step (c). The volume thus sampled may be considerably less than the volume of the capillary, while remaining controllable.

In addition, this quantity may be sampled and discharged without residual microdroplets, on the introduction/emptying orifice side.

As already stated, the process according to the invention can be implemented for obtaining controlled dilutions, especially successive or "cascade" dilutions, from the sample taken and discharged in metered manner by the capillary cavity. By virtue of the microsamples obtained according to the invention, it is possible to obtain infinitesimal dilutions in a precise manner and without handling large quantities of liquid or diluent, which constitutes a decisive advantage of the present invention.

The process according to the invention can be used both for transferring a metered quantity of a liquid, especially a microquantity, to a vessel, or a support such as slide, film, well, cell or the like.

The process according to the invention can be used for adding a metered microquantity of a liquid to a larger, also metered, quantity of the same liquid.

Finally, the process according to the invention can be implemented automatically, with a suitable automated machine.

BRIEF DESCRIPTION OF THE DRAWINGS

The present invention is now described with reference to the attached drawing, in which.

DETAILED DESCRIPTION OF PREFERRED EMBODIMENTS

According to FIGS. 1 to 5, the dimensions of the capillary cavity or tube 1, have been intentionally enlarged, so as to make the following explanations clearer.

Figure 1:
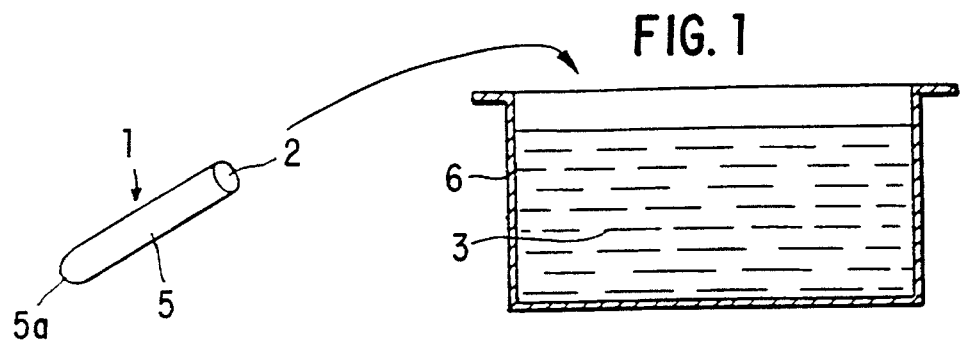
FIGS. 1 to 5 represent, schematically and in its general form, the various steps of a metering process according to the invention.

In general, a metering device according to the invention, while making it possible to sample and then discharge a predetermined quantity of a liquid, comprises:

- a metering device or support 5, represented in FIG. 1, in the form of a capillary tube with a bottom or closed end 5a, used for sampling then releasing the liquid. This support 5 defines or comprises a capillary cavity 1 capable of containing the liquid, outwardly emerging via an orifice 2 for introducing and then emptying the liquid, dimensioned such that the liquid cannot enter or leave said cavity spontaneously. The orifice 2 preferably has a transverse dimension, such as diameter, which is smaller than the mean transverse dimension of the capillary cavity 1 along its length,

- a container or cell 6 capable of containing a bath 3 of the liquid to be metered, and receive the support 5, the interior of the capillary cavity 1 of which can therefore communicate with the interior of the container 6 via the orifice 2. A lid or stopper 7 is capable of closing the container 6 in leaktight manner so as to make a gaseous atmosphere above the liquid bath 3, the pressure of which atmosphere can be controlled. The lid or stopper 7 is equipped with a device 12 for depressurizing and/or pressurizing, for example by connection to the atmosphere, and with a device 13 for introducing and/or removing the liquid, the bottom end of which can be extended as far as the level of the bottom of the container 6, so as to be capable of emptying the container down to this lower level.

According to FIG. 1, the capillary cavity 1, closed at one end 5a and open at one end 2, and the bath 3 of the liquid to be metered, for example of a liquid to be diluted, are therefore provided at the start.

Figure 2:
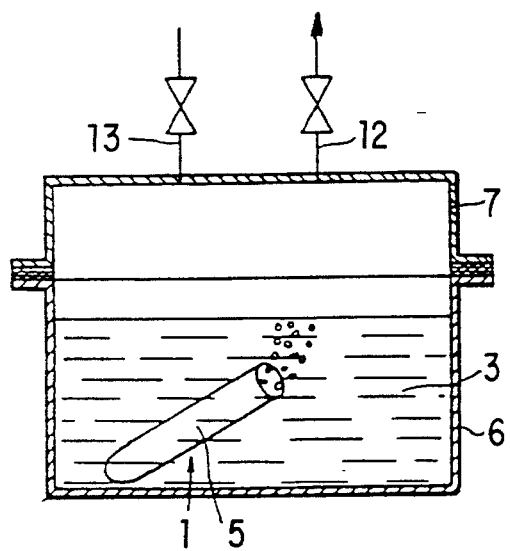

According to FIG. 2, the capillary support 5, and consequently the capillary cavity 1, are introduced into the liquid bath 3. The lid or stopper 7 is arranged on the container 6 and connected to a vacuum source (not shown) via the device 12, the cavity 1, which is initially free of any liquid, is evacuated to bring its internal pressure to a residual value less than that prevailing above the liquid bath 3 during the following step described with reference to FIG. 3, namely atmospheric pressure.

Figure 3:
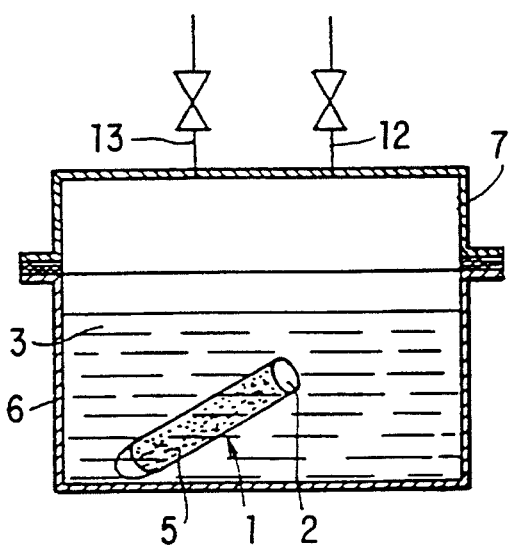

According to FIG. 3, still using the device 12, atmospheric pressure is reestablished inside the enclosure defined by the container 6 and the lid 7, by thereby filling the capillary cavity 1 by connecting the interior of the latter via the orifice 2 to the liquid bath 3. The liquid progresses inside the tube 1 in capillary manner, with a meniscus moving toward the bottom 5a of the capillary cavity 5. The final position of this meniscus depends on the residual pressure obtained at the end of the step according to FIG. 3. The volume sampled by the capillary cavity 1 essentially depends, for a volume of the cavity greater than the volume to be sampled, on its residual internal pressure before filling.

Figure 4:
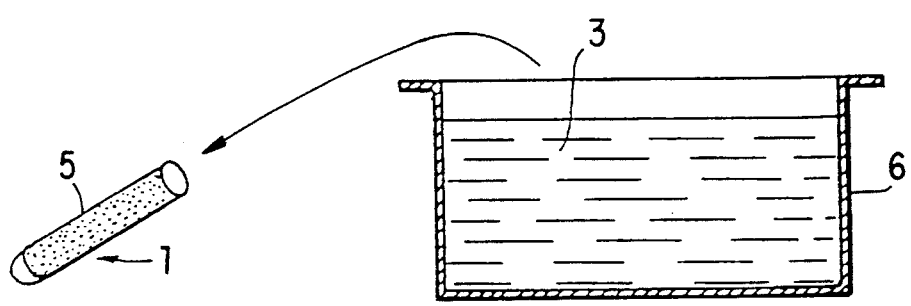

With reference to FIG. 4, the filled cavity 1 is separated from the rest of the liquid bath 3. As indicated above, this separation might be obtained by emptying the interior of the container 6 by the device 13 extended to the bottom of the container 6.

Figure 5:
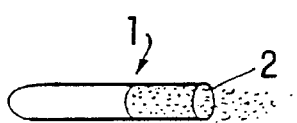

According to FIG. 5, the filled cavity 1, separated from the liquid bath 3, is emptied by any suitable mode, for example:

- application of a centrifugal force passing through the orifice 2;

- application, outside the cavity 1, of an external pressure less than the internal pressure inside said cavity;

- application, inside the cavity 1, of a pressure greater than its internal pressure;

- application of a thrust on the liquid volume filling the cavity 1, toward the outside of the latter.

The liquid progresses out of the tube 1 also in capillary manner, with a meniscus moving toward the orifice 2 of the capillary cavity 5 and leaving the latter.

According to FIG. 2, the evacuation of the capillary cavity 1, prior to its filling with the liquid, is carried out by arranging this cavity in contact with the liquid bath 3, via its orifice 2, and by applying above the bath 3 a pressure less than that prevailing above the bath 3, during the following step described with reference to FIG. 3, namely atmospheric pressure. Clearly, this evacuation could be obtained outside the liquid bath, for example by arranging the support 5 within the enclosure defined by the leaktight joining of the container 6 and the lid 7, by evacuating air from the enclosure then by introducing the liquid bath 3 therein.

It results from the above description that:

- the device for evacuating the capillary cavity 1 of the metering device 5, which is initially free of any liquid, via its orifice 2, is the depressurization device 12;

- the device for separating the capillary cavity 1 filled with liquid from the rest of the liquid bath 3 may be the device 13 for extracting the liquid, used in particular as a device for pumping the latter.

In order to carry out controlled dilution, especially microdilution, after the step according to FIG. 4, the capillary cavity 1 filled with liquid to be diluted is arranged in contact with another liquid bath, namely of the diluent, this being done via the orifice 2, and this filled cavity 1 is emptied, within or into the other liquid bath, namely a determined, preferably metered, quantity of the diluent, for example by applying a pressure less than the internal pressure of the cavity 1 above the diluent bath, as described hereinabove.

The same container or vessel 6, equipped with its lid or stopper 7, can be used for receiving both the liquid to be diluted and the liquid diluent.

Figure 14:
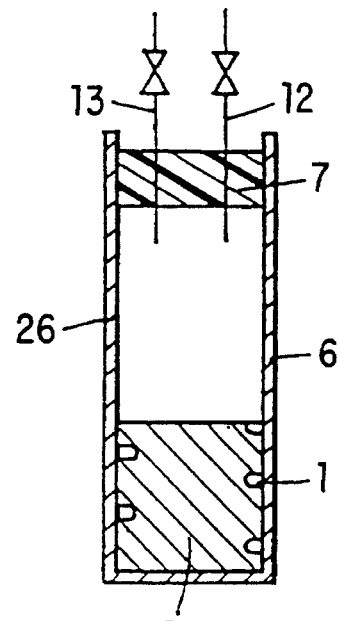
FIG. 14 schematically represents an experimental device which enables testing and quantifying the principles according to the invention.

The efficiency of the principle of metering, and optionally diluting, described above has been tested using the device represented in FIG. 14, which allows metering by spectrophotometry. In this figure, the reference numbers which are identical to those already used with reference to FIGS. 1 to 5 denote the same functional elements or components. According to FIG. 14, the capillary cavity 1 is obtained by having made, by any suitable means, for example by machining, a helical groove on the external surface of a cylindrical core 25, which is arranged in leaktight manner at the bottom of the cylindrical wall of a tube 26; the helical groove emerges into the container 6 defined by the free volume in the tube 26 and is closed at its opposite end.

By way of example, the container 6 constitutes a volume of 7 ml and the helical capillary cavity 1 constitutes a volume of 55 µl. The walls of the tube 26 are transparent, so as to allow optical measurements, and in particular optical density measurements.

With this experimental device, the following operational mode is implemented:

initially, the helical capillary cavity 1 is empty of liquid, and especially at atmospheric pressure; it cannot be filled by capillary action alone in contact with the liquid to be metered the container 6 receives a solution comprising ink or a dye diluted in demineralized water, in a proportion of one volume of ink per hundred volumes of water; this solution constitutes the initial liquid bath using the device 12, which may comprise of a simple syringe passing through the stopper 7, the container 6 is depressurized by sucking out a predetermined volume of air; this evacuates the air from the capillary cavity 1, to the extent that the latter is also depressurized to a controlled residual internal pressure still using the device 12, the interior of the cavity 6 returns to atmospheric pressure, by means of which the capillary cavity 1 is filled with the solution the excess solution is extracted from the container 6, for example by pumping or simple draining, and the interior of the container 6 is washed with demineralized water, at atmospheric pressure, so as to prevent any entry of washing liquid into the capillary cavity 1 and/or exit of liquid from the cavity 2 ml or any other volume of a diluent, for example the demineralized water, are then introduced into the container 6, in order to form the other liquid bath in the sense of the above general definition the container 6 is then depressurized, using the same device 12, by means of which the initial ink solution trapped by the capillary cavity 1 is extracted into the container 6, in order to obtain a mixture of the diluent and of this initial solution 1 ml of this mixture is sampled and determined on a "Reaction Rate Photometer" spectrophotometer marketed by the company VITATRON, for an optical density reading at 620 nm the cycle described above may be repeated a plurality of times, the mixture obtained at the end of the preceding cycle constituting the starting liquid bath of the following cycle.

By calibration of the spectrophotometer, it is possible to correlate the optical density of each dilution or sub-dilution and the ink concentration of the latter. For a given dilution, five different operations are carried out, in order to obtain a mean value.

For all these experiments, the Table No. 1 below is obtained, in which:

the first column expresses, in %, the theoretical concentration of primary or starting solution of the optically determined mixture, obtained from the number of dilutions and/or from the volume of the diluent used the second column expresses the optical density of the mixture alone, expressed in ODm the third column expresses the standard deviation the fourth column expresses the coefficient of the variation

TABLE NO. 1

| conc (%) | ODm | SD | CV |
|---|---|---|---|
| 0.1 | 6.6 | 0.5 | 8.2% |
| 0.2 | 11.8 | 1.1 | 9.3% |
| 0.4 | 20.8 | 2.1 | 10% |
| 0.6 | 32.2 | 3.2 | 10% |
| 0.8 | 40.8 | 1.5 | 3.6% |
| 0.9 | 45.6 | 0.5 | 1.2% |
| 0.95 | 47.5 | 1.2 | 2.6% |
| 1 | 50.6 | 2.4 | 4.7% |
| 1.5 | 73.4 | 1.5 | 2% |
| 1.75 | 86 | 1.4 | 1.6% |
| 2 | 92 | 1 | 1% |
| 2.25 | 108 | 1.6 | 1.5% |
| 2.5 | 120.4 | 2.5 | 2.1% |
| 3 | 139.4 | 2.3 | 1.6% |

OPTICAL DENSITY AS A FUNCTION OF THE PRIMARY SOLUTION CONCENTRATION

By correlating these values, plotting the concentrations on the abscissa and the optical densities on the ordinate, an almost linear correlation is observed between the concentration and the optical density, according to the following law:

$$ODm = \text{concentration (in \%)} \times 46 + 3.5$$

with a linear correlation coefficient r=0.9992.

It was then sought to determine the influence of the residual internal pressure at the end of emptying the capillary cavity on the precision or value of the liquid volume sampled then discharged by this cavity.

According to Table No. 2, a liquid bath or primary solution of ink in water is started with, the volume of which is given in ml as indicated in the first column. Each operation is carried out five times at a determined pressure, and the values expressed hereinbelow correspond to the mean.

TABLE NO. 2

| ml | ODm | SD | CV | dilution (%) |
|---|---|---|---|---|
| 1 | 20 | 7 | 36% | 0.35 |
| 2 | 38 | 3 | 7% | 0.75 |
| 3 | 51 | 6 | 12% | 1.03 |
| 4 | 58 | 3 | 6% | 1.18 |
| 5 | 70 | 3 | 4% | 1.45 |

OPTICAL DENSITY AND DILUTION AS A FUNCTION OF REDUCED PRESSURE

According to Table No. 3 the same operations are carried out as were defined with reference to Table No. 2, but by using a vacuum source monitored using a manometer, the value of the setting of which, expressed in millibars, is given in the first column of Table No. 3 below.

TABLE NO. 3

| mBar | ODm | SD | CV | dilution (%) |
|------|-------|------|-----|--------------|
| 50 | 4.6 | 1.8 | 39% | 0.024 |
| 75 | 8.8 | 0.8 | 9% | 0.115 |
| 100 | 11.2 | 1.3 | 12% | 0.167 |
| 150 | 19.4 | 1.14 | 6% | 0.346 |
| 200 | 28 | 2.1 | 8% | 0.532 |
| 270 | 37.2 | 1.8 | 5% | 0.733 |
| 300 | 43.4 | 1.8 | 4% | 0.867 |
| 400 | 57.2 | 2.7 | 5% | 1.167 |
| 500 | 70.8 | 1.6 | 2% | 1.463 |
| 600 | 82.6 | 2.4 | 3% | 1.719 |
| 700 | 95.8 | 1.9 | 2% | 2.007 |
| 800 | 120.2 | 1.6 | 1% | 2.537 |

OPTICAL DENSITY AND DILUTION AS A FUNCTION OF REDUCED PRESSURE (THE VALUES WERE CALCULATED ON THE BASIS OF THE ABOVE LINEAR CORRELATION)

As a conclusion for these Tables No. 2 and 3, it is observed that, when the residual internal pressure before filling is less than 400 millibars, the dilution remains proportional to the residual pressure. Above this value, the dilution tends toward a limit which corresponds to the approximation of total vacuum in the capillary cavity.

Figure 6:
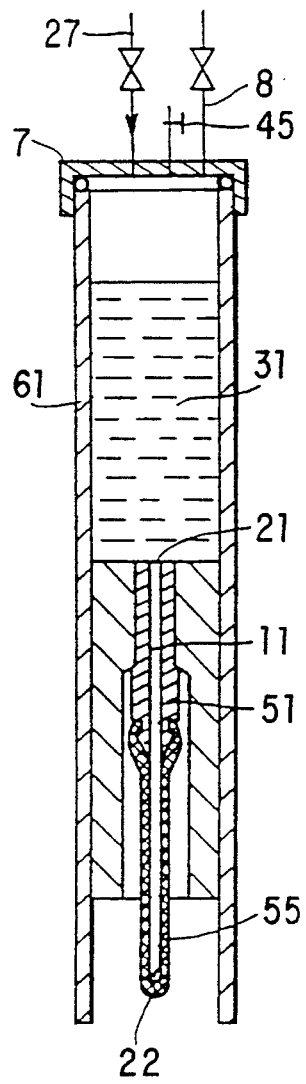
FIGS. 6 to 8 represent, schematically and using an automatic device, a first embodiment of a process for metering microvolumes according to the invention, for example within the scope of an automatic bacteriology apparatus or machine.
Figure 7:
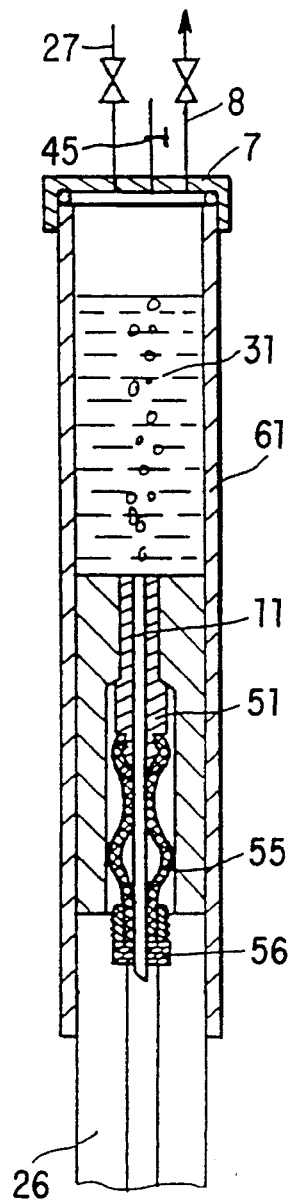
Figure 8:
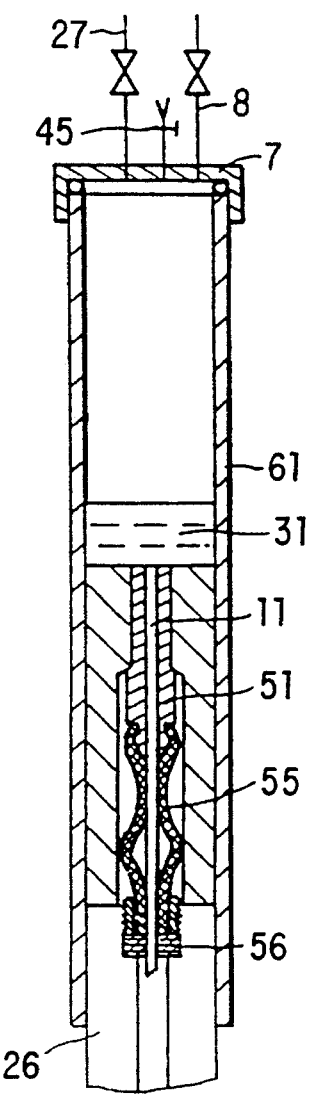

According to FIGS. 6 to 8, a schematic description is given of a first mode of metering a liquid according to the invention, using a tube 61 ending in a perforating needle 51 closed by a septum 55 defining a straight capillary conduit 11, which includes two orifices 21 and 22, the first 21 on the tube 61 side and the second 22 on the needle 51 outlet side; it is to be understood that the diameter of the orifice 22 can vary, in so far as it allows a capillary regime to be maintained. Such a tube is intended to interact with a hollow vessel or cassette or card 26, closed by an introduction valve 56, including a viscoelastic perforable capsule. A stopper 7 closes the upper part of the tube 61 and is equipped with a device 8 connected to a vacuum source, with a device 27 connected to a supply of solution to be metered and diluted, a device 28 (represented only in FIG. 10) for pumping inside the tube 61, and a device 45 for connecting the inside of the tube 61 to the atmosphere.

Figure 10:
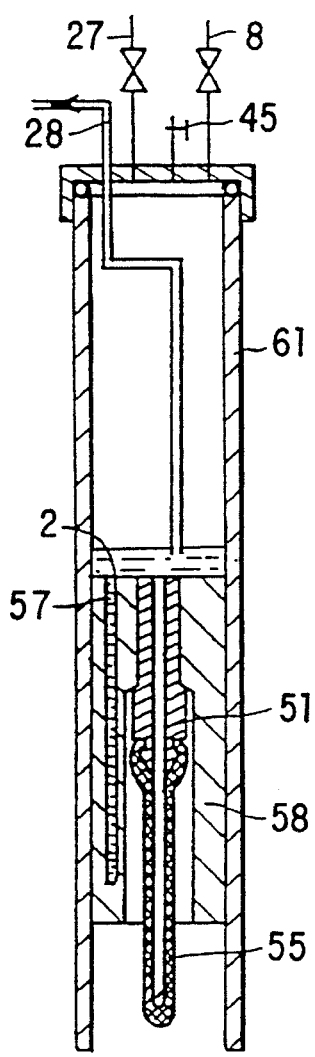

In an automated biological measurement machine, especially for bacteriology, according to the first embodiment of the invention, the following steps are implemented; in order successively to fill a cassette with the liquid to be diluted and another cassette with the same liquid diluted in a diluent:

according to FIG. 6, the tube 61 is filled with a quantity, given in ml, of a liquid 31 to be diluted;

according to FIG. 7, the needle 51 penetrates into the valve 56 in leaktight manner, the interior of the filled tube 61 is placed under at least partial vacuum so as, on the one hand, to evacuate the air contained in the capillary cavity 11 of the perforating needle 51 and, on the other hand, at least partially to evacuate the air from the cassette 26;

according to FIG. 8 and still with the needle 51 penetrating into the valve 56, atmospheric pressure being reestablished inside the tube 61, the cassette 26 is filled with a predetermined volume of the liquid to be diluted;

once the cassette 26 has been filled, the tube 61 is withdrawn with respect to the cassette 26, the perforating needle 51 is again closed at one end by the septum 55, and the capillary cavity 11 thus traps a determined quantity of liquid to be diluted;

the residual volume 31 in the tube 61 is removed, for example by means of the conduit 28 represented in FIG. 10 and connected to a vacuum source;

the tube 61 is filled with a determined quantity of diluent, as already described with reference to FIG. 6;

as already described with reference to FIG. 7, the needle 51 penetrates into the valve 56 of a new cassette, and the interior of the tube 61 filled with diluent is placed under at least partial vacuum, in order at least partially to evacuate the air contained in the new cassette and empty the liquid to be diluted contained in the capillary cavity 11, thus diluting the latter;

as already described with reference to FIG. 8, the new cassette is filled with the dilution obtained.

According to FIGS. 9 to 13, a second embodiment of the invention is implemented, for which the means previously described with reference to FIGS. 6 to 8 are modified, in order to provide a straight and blind capillary cavity 57 within the core 58 closing the tube 61, communicating with the upper part of the latter.

Figure 9:
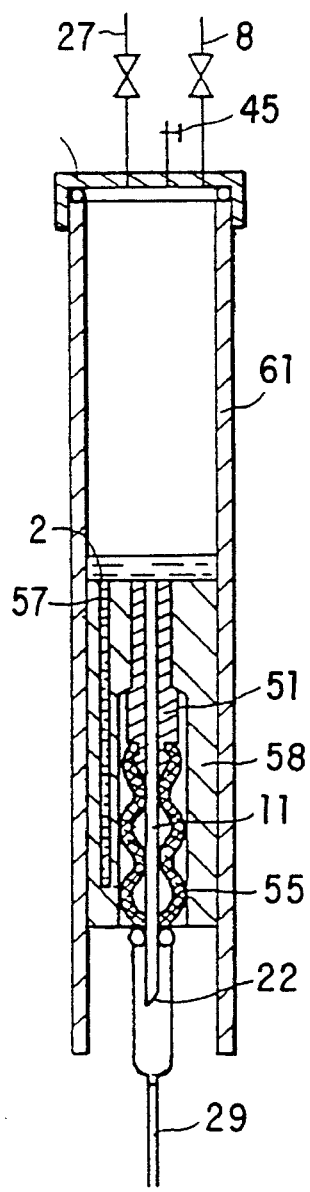
FIGS. 9 to 13 represent, still schematically, and using an automatic device, a second embodiment of a process for metering microvolumes according to the invention, implemented in order to carry out controlled dilution, still within the scope of an automated bacteriology machine.

The starting point is the state represented in FIG. 9 or 10, according to which the cavity 57 has been filled with the liquid to be diluted, and a residual quantity of the same liquid is present in the tube 61. This state can be obtained by carrying out the steps previously described with reference to FIGS. 6 to 8.

Figure 11:
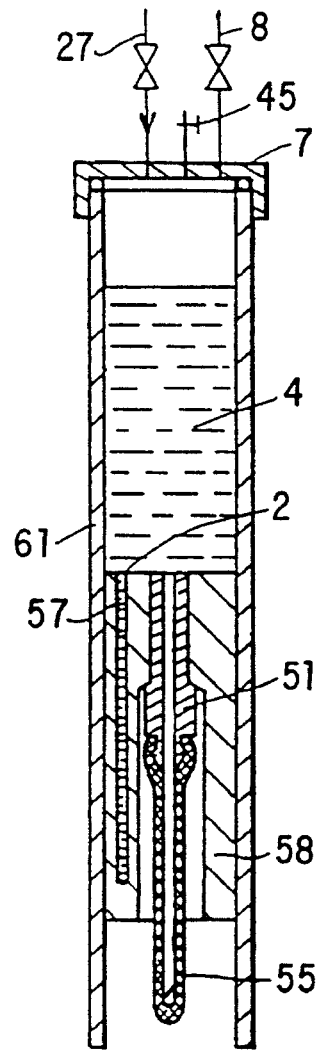
Figure 12:
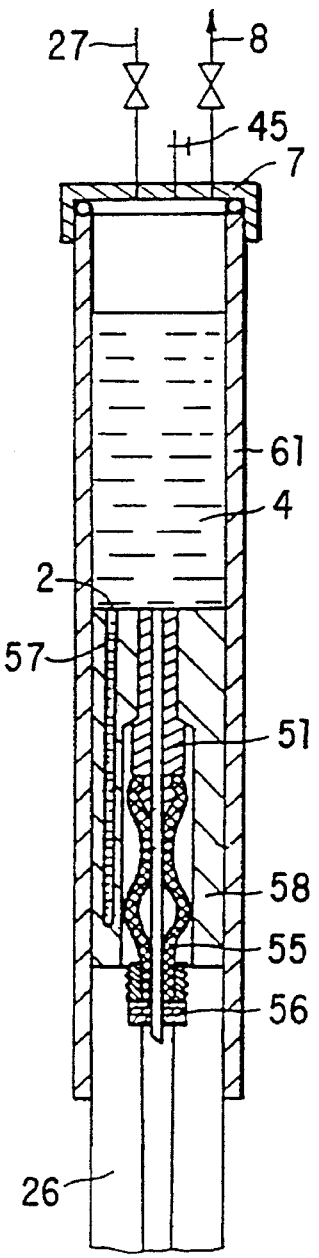
Figure 13:
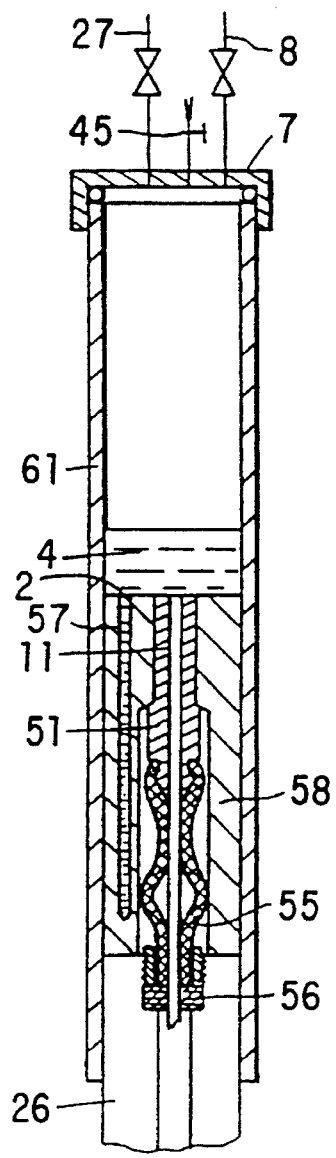

Starting from this state, the following steps are carried out:

according to FIG. 9, the perforating needle 51 is emptied via its downstream end 22, with perforation of the septum 55, by virtue of a vacuum source 29 applied in leaktight manner to the bottom end of the needle 51, until the tube 61 and the needle 51 are completely emptied, the cavity 57 remaining full;

or, according to FIG. 10, without perforation of the septum 55, the liquid inside the tube 61 is pumped, until the tube 61 is emptied, the cavity 57 remaining full; clearly, in this embodiment, it is impossible to empty the needle 51; in addition, in order not excessively to disturb the precision of the dilution, it is imperative for the volume of the needle 51 to be practically negligible with respect to the volume of the cavity 57; this can be obtained with a helical capillary cavity according to the embodiment described in FIG. 14; and the tube 61 should be emptied under atmospheric pressure in order not to create a pressure reduction, even a partial and/or temporary one, which might even partially empty the cavity 57 via the conduit 28 connected to a vacuum source (not shown);

according to FIG. 11, the interior of the tube 61 is then filled with a diluent by the device 27 according to FIG. 12, by connection between the needle 51 and the valve 56, the interior of the tube 61 and of the cassette 26 are depressurized, by means of which the capillary cavity 57 discharges within the diluent the quantity of liquid to be diluted previously trapped in this same cavity; mixing and dilution therefore take place;

according to FIG. 13, by connecting the interior of the tube 61 to the atmosphere, and by establishing a link between the needle 51 and the interior of the cassette 26, the diluted volume thus obtained is emptied into the cassette.

I claim:

1. A process for metering a predetermined quantity of a liquid, comprising the steps of:

(a) providing at least one capillary cavity that is capable of containing said liquid, the at least one capillary cavity having an outwardly emerging orifice that is used for introducing and emptying said liquid, the outwardly emerging orifice being dimensioned such that the liquid cannot enter or leave said cavity spontaneously;

(b) providing a body of said liquid;

(c) evacuating said cavity via the orifice, initially free of any liquid, at least partially in order to bring a residual internal pressure of said cavity to a value which is less than a pressure prevailing on the liquid body during step (d);

(d) communicating the interior of the at least partially evacuated capillary cavity to the liquid body via the orifice, and subsequently introducing into said cavity a predetermined volume of said liquid in said liquid body;

(e) separating the capillary cavity from a remainder of the liquid body;

(f) emptying only the predetermined volume of said liquid contained in said capillary cavity via the orifice, which has been separated from the liquid body.

2. The process according to claim 1, wherein the evacuating step comprises arranging said cavity in the liquid body and applying on the liquid body a pressure less than a pressure prevailing on the liquid body during said communicating step.

3. The process according to claim 1, wherein the emptying step further comprises one of:

3.1 applying a centrifugal force passing through the introduction orifice;

3.2 applying, outside the cavity, an external pressure less than the cavity's internal pressure;

3.3 applying, inside the cavity, a pressure greater than the cavity's internal pressure; and 3.4 pushing out the predetermined volume of the liquid in the cavity.

4. The process according to claim 3, wherein step 3.2 comprises arranging the cavity in a liquid bath and applying a pressure less than the internal pressure of the cavity on said liquid bath.

5. The process according to claim 4, wherein the predetermined volume of liquid in the cavity comprises a liquid to be diluted, and the emptying step further comprises emptying the predetermined volume of liquid in the cavity into a metered quantity of a liquid diluent.

6. The process according to claim 5, wherein the metered quantity of the liquid diluent constitutes said liquid bath.

7. The process according to claim 1, further comprising providing the orifice with a cross-sectional dimension that is less than a cross-sectional dimension of the capillary cavity.

8. The process according to claim 1, wherein the evacuating step includes partially evacuating the cavity to a value that is less than atmospheric pressure.

9. The process according to claim 1, wherein communicating the interior of the capillary cavity to the liquid bath occurs under atmospheric pressure conditions.

10. A device for metering a predetermined quantity of a liquid, comprising:

(A) a metering means for sampling and releasing the liquid, the metering means comprising a capillary cavity capable of containing a predetermined volume of said liquid, the cavity having an outwardly emerging orifice that is used for introducing and emptying said liquid, said orifice being dimensioned such that the liquid cannot enter or leave said cavity spontaneously;

(B) a container capable of containing a body of said liquid, whereby an interior of the body of said liquid can communicate with an interior of the cavity of the metering means via the orifice of the cavity;

(C) means for evacuating the cavity of the metering means via the orifice;

(D) means for separating the cavity of the metering means having the predetermined volume of said liquid from a remainder of the liquid body; and (E) means for emptying, via said orifice, only said predetermined volume of said liquid in the cavity which is separated from the body.

11. The metering device according to claim 10, wherein the evacuation means comprises means for depressurizing the gaseous atmosphere above the body.

12. The metering device according to claim 10, wherein the means for separating the cavity from the remainder of the liquid body is one of a means for pumping the liquid body remainder and means for suction of the liquid body remainder through a calibrated orifice of the cavity.

13. The metering device according to claim 10, wherein the means for emptying the cavity filled with liquid comprises means for applying a pressure less than the cavity's internal pressure to said cavity.

14. The metering device according to claim 10 wherein the orifice has a transverse dimension that is less than the mean transverse dimension of the capillary cavity, along its length.

15. The metering device according to claim 14, wherein the transverse dimension of said orifice is a diameter.

16. The metering device according to claim 10, wherein the body of said liquid is a liquid to be diluted, and the container is adapted to receive the liquid to be diluted and, subsequently, a liquid diluent.

17. The metering device according to claim 16, wherein the container communicates with means for one of pressurizing and depressurizing said cavity, and means for one of introducing and removing the liquid to be diluted.

18. The metering device according to claim 10, wherein the metering means comprises a needle that defines the capillary conduit and includes two orifices, one orifice communicating with the container and the other orifice communicating with atmosphere.

19. The metering device according to claim 18, further comprising a vessel that communicates with the other orifice.

20. The metering device according to claim 10, wherein the metering means further comprises a support integral with said capillary cavity.

21. The metering device according to claim 10, wherein the orifice has a cross-sectional dimension that is less than a cross-sectional dimension of the capillary cavity.

* * * * *